United States Patent
Nakajima et al.

(10) Patent No.: US 7,016,021 B2
(45) Date of Patent: Mar. 21, 2006

(54) METHOD FOR MEASURING CONCENTRATION OF COMPONENT CONTAINED IN BODILY FLUID AND APPARATUS FOR MEASURING CONCENTRATION OF COMPONENT CONTAINED IN BODILY FLUID

(75) Inventors: Satoshi Nakajima, Kyoto (JP); Muneo Tokita, Kyoto (JP); Yusaku Sakoda, Kyoto (JP)

(73) Assignee: Omron Corporation, Kyoto (JP)

( * ) Notice: Subject to any disclaimer, the term of this patent is extended or adjusted under 35 U.S.C. 154(b) by 290 days.

(21) Appl. No.: 10/440,423

(22) Filed: May 19, 2003

(65) Prior Publication Data

US 2004/0012788 A1 Jan. 22, 2004

(30) Foreign Application Priority Data

Jun. 19, 2002 (JP) ...................................... 2002-177902

(51) Int. Cl.
*G01N 1/00* (2006.01)
*A61B 5/00* (2006.01)

(52) U.S. Cl. ......................................... 356/39; 600/316
(58) Field of Classification Search ............. 356/39–42, 356/128–137, 335–343, 445–448; 600/309–310, 600/316–324, 345–352, 365
See application file for complete search history.

(56) References Cited

U.S. PATENT DOCUMENTS

| 5,313,264 | A | | 5/1994 | Ivarsson et al. ............... 356/73 |
| 5,533,509 | A | * | 7/1996 | Koashi et al. ............... 600/316 |
| 5,696,580 | A | | 12/1997 | Kubo et al. .................... 356/72 |
| 6,493,090 | B1 | | 12/2002 | Lading et al. ............... 356/484 |

| 2005/0002031 | A1 | * | 1/2005 | Kraemer et al. ............ 356/337 |
| 2005/0010090 | A1 | * | 1/2005 | Acosta et al. ................ 600/316 |

FOREIGN PATENT DOCUMENTS

WO WO 95/09355 4/1995

OTHER PUBLICATIONS

Z. Trajanoski "Continuous Ex Vivo Monitoring of Glucose in Blood and Subcutaneous Tissue Fluid" 1994, IEEE, 0-7803-2050-6/94.*
Martin Ellmerer "Continuous Monitoring of Lactate in Subcutaneous Adipose Tissue During Excercise Using Open Flow Micoperfusion" 1997, IEEE, 0-7803-3811-1/97.*
D.w Kim "Importance of Skin Resistance in the Reverse Iontophoresis–based Non–invasive Glucose Monitoring System" 2004, IEEE, 0-7803-8439-3/04.*

* cited by examiner

*Primary Examiner*—Michael P. Stafira
(74) *Attorney, Agent, or Firm*—Morrison & Foerster LLP

(57) ABSTRACT

A measuring unit is placed at the surface of a living body. The pressure inside of a glass container is reduced by a pressure reducing tank, so that a subcutaneous exuding fluid is taken out at the surface of the living body from under a skin. The subcutaneous exuding fluid is allowed as a sample to be measured to reach a metallic film through porous molecular weight selective films. A light beam emitted from a light source passes through a prism, and then, is reflected on the metallic film, and finally, is received on a linear array sensor. A minimum intensity position on the linear array sensor, generated by surface plasmon resonance is obtained, and then, a resonant angle is detected. The concentration of substance to be measured contained in the sample to be measured is calculated based on the resonant angle and position. Thus, the concentration of a component contained in a bodily fluid can be readily measured for a long time of period in a continuous manner without any special treatment by taking a very small quantity of exuding fluid without any pain.

18 Claims, 18 Drawing Sheets

PRIOR ART 0.2mm 0.5mm

PRIOR ART

METHOD FOR MEASURING CONCENTRATION OF COMPONENT CONTAINED IN BODILY FLUID AND APPARATUS FOR MEASURING CONCENTRATION OF COMPONENT CONTAINED IN BODILY FLUID

BACKGROUND OF THE INVENTION

1. Field of the Invention

The present invention relates to a method for measuring the concentration of a component contained in a bodily fluid of a living body and a measuring apparatus therefor. More particularly, the present invention relates to a method and an apparatus for taking a bodily fluid from a living body and measuring the refractive index of a component contained in the bodily fluid by the use of, for example, a surface plasmon resonator device so as to measure the concentration of the component contained in the bodily fluid of the living body.

2. Description of the Background Art

A diabetic or the like has conventionally measured a blood sugar value a plurality of times every day by himself or herself. In such measurement, he or she has taken a blood sample from his or her capillary by using a blood taking tool, and then, has measured the blood sugar value by himself or herself by means of a sensor and measuring instrument exclusive for the measurement.

However, the measurement of the blood sugar value by the diabetic by himself or herself has raised many problems such as a pain at the time of taking the blood every time, hardening of a skin through which the blood is taken and a danger of infection. Therefore, the diabetic who measures the blood sugar value every day has had great expectations of an improvement in a blood sugar value measuring method.

The concentration of a component contained in an intercellular fluid in subcutaneous tissue (i.e., a fluid resulting from the filtration of blood through the wall of a capillary) has a good correlation with the concentration of the blood. In view of this, in recent years, the blood has not been measured, but the intercellular fluid in the subcutaneous tissue is exuded to the surface of the skin from under the skin (hereinafter referred to as "a subcutaneous exuding fluid"). The resultant fluid has been used as a sample to be measured. There have been proposed several measuring methods by which the above-described problems can be solved.

As methods for taking the subcutaneous exuding fluid, there have been proposed a method by means of a small-sized syringe needle and a method by using a laser beam.

In the method by means of a small-sized syringe needle, a small-sized syringe needle 1 has been allowed to be shallowly invaded, thereby taking a subcutaneous interstitial fluid, as shown in FIG. 16. A quantity of fluid taken at a time in this method has been about 1 $\mu$L. FIGS. 17A and 17B illustrate the case where a plurality of syringe needles 1 have been used.

In the method by using the laser beam, a fine pore has been formed by irradiating the surface of a skin with a laser beam of minute power, and then, a subcutaneous exuding fluid has been taken through the fine pore. With the laser beam of minute power, it has been possible to remarkably alleviate the pain to a living body.

In the meantime, examples of a method for measuring a very small quantity of a sample such as the subcutaneous exuding fluid include an enzyme reagent method and enzyme electrode methods.

The enzyme reagent method is a method for supplying a sample to be measured to a reaction reagent layer in which an enzyme and a color reagent are mixed together and optically measuring a change in color so as to calculate a concentration. A sample of about 3 $\mu$L is needed.

The enzyme electrode method is a method for forming a reagent layer containing an enzyme therein directly on a plurality of electrodes made of carbon or noble metal, supplying a sample to be measured on the resultant reagent layer, decomposing a product resulting from an enzyme reaction by means of the electrodes with the application of a potential, and converting a change in decomposition current quantity into a measurement value by using a special-purpose algorithm.

Alternatively, another enzyme electrode method is a method for forming a reagent layer containing an enzyme therein on a reference electrode made of noble metal or the like and an FET gate which is exposed, supplying a sample on the resultant reagent layer, measuring a change in pH resulting from an enzyme reaction as a change in gate potential, and converting the change into a measurement value by using a special-purpose algorithm.

However, the methods for taking the subcutaneous exuding fluid and the methods for measuring a very small quantity of sample in the prior art described above have raised problems as follows:

First, the method for taking the subcutaneous exuding fluid by the use of the small-sized syringe needle causes a pain since the small-sized syringe needle pierces the skin, causes a danger of infection, and takes time for curing the skin. Moreover, the skin of a human being generally has an excellent elasticity, so that the skin dimples when the needle 1 is intended to be shallowly pierced. Therefore, the invasion depth of the needle 1 is varied per piercing, thereby making a taking quantity inconstant. In the case of the great depth, the blood is mixed with the sample, blood cells adversely influence on measurement accuracy.

It has been conceived that the numerous small-sized syringe needles are arranged so as to stabilize the piercing depth and alleviate the pain in the other method by the use of the small-sized syringe needles, as illustrated in FIGS. 17A and 17B. However, there have arisen problems of a danger that the needle is broken in the skin caused by a decrease in strength of the needle and an increase in fabricating cost.

Next, in the method using the laser beam, it is, indeed, possible to alleviate the pain by using the laser beam of low power, but the subcutaneous exuding fluid cannot be naturally exuded from the fine pore formed at the surface of the skin by the use of the laser beam. The subcutaneous exuding fluid must be forcibly exuded, and therefore, the taking quantity is small. Moreover, the power control of the laser beam is difficult from the technical viewpoint, and further, it is difficult to cope with the states of skins different individually. Although the irradiation of the laser beam a plurality of times may be conceived by adding a feedback function to the power control, operability is reduced in this case.

The method for measuring the very small quantity of sample in the prior art has raised problems as follows:

First, in the enzyme reagent method, the entire quantity of sample required for the reaction is needed at the time of the beginning of the measurement. In the case where the subcutaneous exuding fluid is gradually taken, a supplying system need be provided for reserving the subcutaneous exuding fluid once, and then, supplying it to a reaction system. Moreover, it is difficult to decrease the quantity of sample in the sample layer or the optical measuring system from the viewpoint of sureness of a quality. In addition, in the enzyme reagent method, the sample is thrown away after one measurement, and therefore, it cannot be continuously measured.

In contrast, although a necessary quantity of sample is about 3 µL in the enzyme electrode method, the entire quantity of sample required for the reaction is needed at the time of the beginning of the measurement. Consequently, a supplying system need be provided similarly to the enzyme reagent method. In addition, also in the enzyme electrode method, the sample is disposed of, and therefore, it cannot be continuously measured.

Additionally, in the method for measuring a change in pH according to an enzyme reaction as a change in gate potential, the sample is indispensably diluted. An apparatus is large in size caused by dilution or calibration. Therefore, the sample is needed in a quantity of 5 µL for one measurement. Furthermore, a supplying system need be provided for reserving the subcutaneous exuding fluid.

SUMMARY OF THE INVENTION

The present invention has been accomplished in an attempt to solve the above problems observed in the prior art. An object of the present invention is to provide a method for measuring the concentration of a component contained in a bodily fluid and an apparatus for measuring the concentration of a component contained in a bodily fluid, in which a very small quantity of bodily fluid such as a subcutaneous exuding fluid can be readily measured for a long period of time, and further, can be continuously measured with an alleviated physical or mental pain of a test subject in comparison with the case where blood is taken and without any reagent or any special treatment for measurement.

In the method for measuring the concentration of a component contained in a bodily fluid according to the present invention, the concentration of a component contained in a bodily fluid is measured by taking a bodily fluid from a living body; separating a sample to be measured from the bodily fluid; measuring the refractive index of the separated sample; and calculating the concentration of substance to be measured based on the refractive index.

Furthermore, in the method for measuring the concentration of the component contained in the bodily fluid according to the present invention, surface plasmon resonance is used in measuring the refractive index.

Moreover, the apparatus for measuring the concentration of the component contained in the bodily fluid according to the present invention comprises: bodily fluid taking means for taking the bodily fluid from a living body; sample separating means for separating a sample to be measured from the bodily fluid taken by the bodily fluid taking means; refractive index measuring means for measuring the refractive index of the sample separated by the sample separating means; and concentration calculating means for calculating the concentration of substance to be measured contained in the sample to be measured or the bodily fluid based on the refractive index measured by the refractive index measuring means.

Additionally, it is specifically preferable that the apparatus for measuring the concentration of the component contained in the bodily fluid according to the present invention should comprise: a light source unit for measurement including at least a light source; a porous molecular weight selective film which is brought into close contact with the surface of a living body; a bodily fluid taking unit for allowing the bodily fluid to be exuded from the surface of the living body, and then, to permeate through the porous molecular weight selective film, thus obtaining a sample to be measured; an optical element for allowing light emitted from the light source unit for measurement to enter into the sample to be measured on the porous molecular weight selective film, and further, for reflecting the light on the sample to be measured; a light receiving element for receiving the light reflected on the sample to be measured, emitted from the optical element; a control unit including a concentration calculator for calculating the concentration of substance to be measured contained in the sample or the bodily fluid in response to a signal output from the light receiving element; and a display unit for displaying the concentration obtained by the concentration calculator.

In addition, the apparatus for measuring the concentration of the component contained in the bodily fluid according to the present invention is provided with a surface plasmon element as the optical element.

DESCRIPTION OF THE PREFERRED EMBODIMENTS

First, reverse iontophoresis and pressure reduction method are adopted as methods for taking a very small quantity of bodily fluid such as a subcutaneous exuding fluid according to the present invention.

The reverse iontophoresis is a method for sticking an electrode to the surface of a skin and inducing the movement of ions in a body with the application of a DC voltage to the electrode in a pulse manner or constantly, so as to exude a bodily fluid outside of the body by an electric attractive force.

Figure 18A:
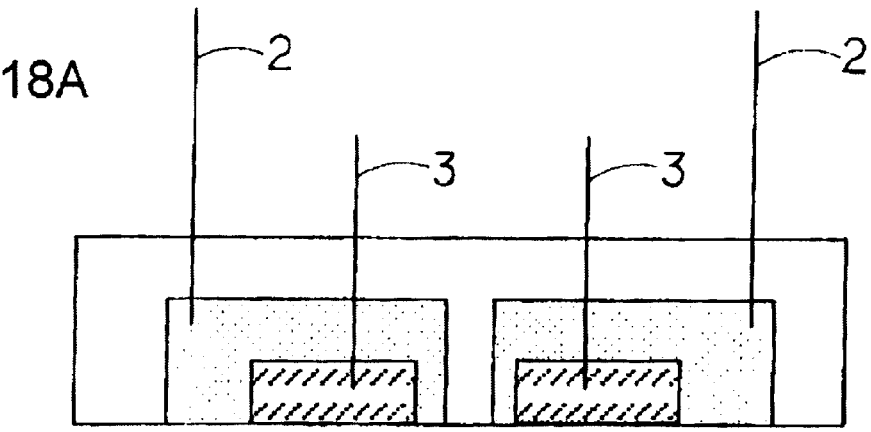
FIGS. 18A and 18B are views illustrating the principle of taking a bodily fluid by reverse iontophoresis.
Figure 18B:
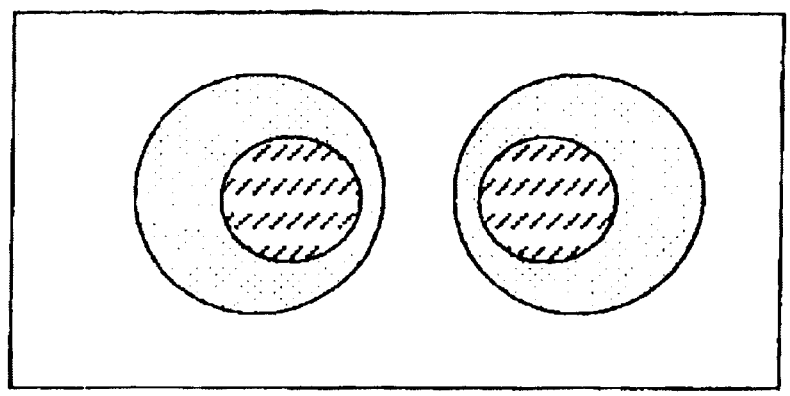

Specifically, as shown in FIG. 18A being a side view and FIG. 18B being a plan view, two subcutaneous exuding fluid inducing electrodes 2 and two sensing electrodes 3 are placed at the surface of the skin. A difference in potential, for example, a DC potential of 0.5 V is repeatedly or constantly applied to between the electrode 2 and the electrode 3, thereby generating movement of an ion compound along a potential gradient. Together with this movement of the ion compound, a subcutaneous bodily fluid is exuded to the surface of the skin. The subcutaneous bodily fluid can be taken in about 2 to 3 $\mu$L/H in the potential applying type.

Next, pressure reduction method is a method for reducing a pressure of a part of the surface of a skin (for example, down to a pressure of about ½ atmosphere, i.e., about 400 mmHg) so as to exude a subcutaneous bodily fluid. The subcutaneous bodily fluid can be taken in about 2 to 3 $\mu$L/10 min/cm$^2$. Little pain is given at a pressure of about ½ atmosphere. Although the surface of the skin at which the subcutaneous bodily fluid is taken is temporarily reddened, it can be completely recovered in about one day.

Hereinafter, the present invention will be described in more detail by way of preferred embodiments. First, a description will be given of an apparatus for measuring the concentration of a component contained in a bodily fluid by using a surface plasmon resonance phenomenon in a first preferred embodiment. Therefore, explanation will be made in advance on the surface plasmon resonance phenomenon.

The surface plasmon resonance phenomenon is generated in a form of an electromagnetic wave (an Evanescent wave) at the surface of a metallic film formed on either surface of glass when light of a single color is incident at a whole reflection angle or more of the glass. When this electromagnetic wave resonates with electron oscillation in a plasma state (a surface plasmon wave) at the metallic surface, the optical energy of the incident light is varied into undulatory energy of surface plasmon. As a result, the intensity of a reflection wave is reduced.

The number of surface waves generated by the surface plasmon resonance phenomenon is influenced by the permittivity of the metallic film and the refractive index (the square root of the permittivity) of a medium in contact with the metallic film. The influence ranges within about several tenths $\mu$m in thickness. Light is allowed to be incident sideways into a prism having the metallic film made of gold (Au) or silver (Ag) at the bottom surface thereof, and then, the refractive index of the adjacent medium is measured by measuring a variation in intensity of the reflection light (i.e., resonant absorption).

Figure 1:
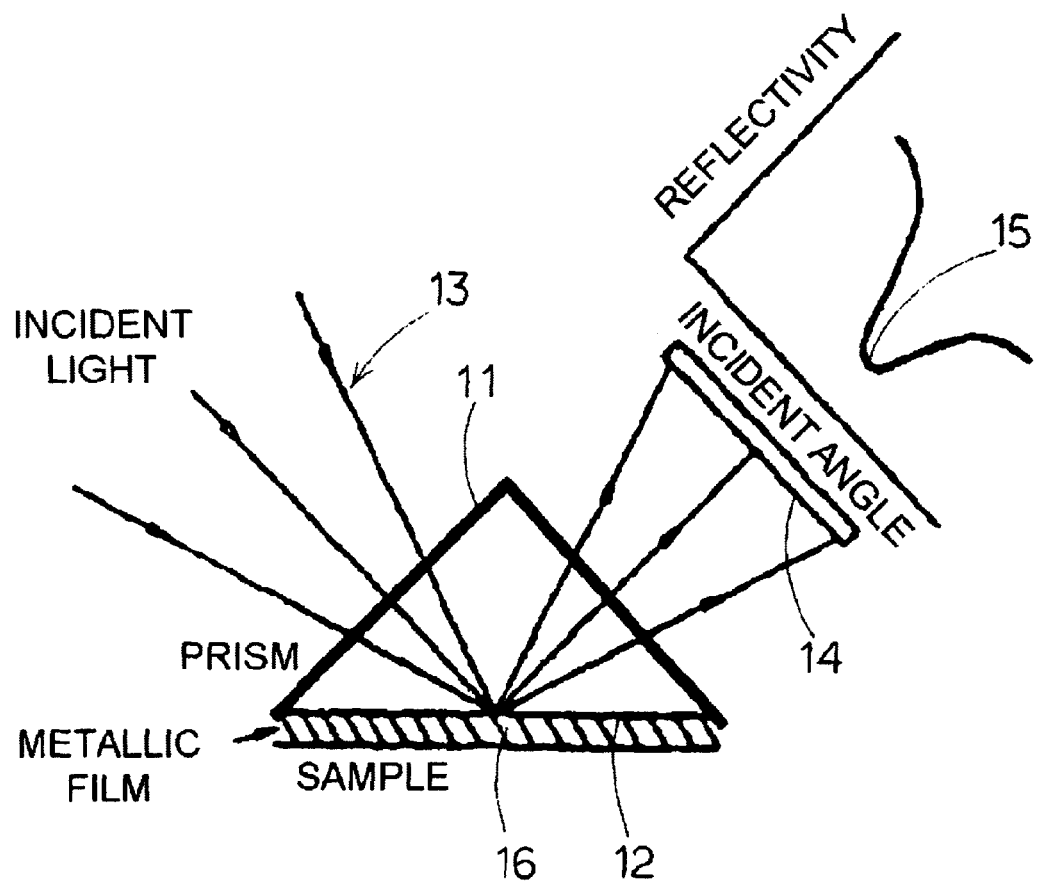
FIG. 1 is a view illustrating the measurement principle of an apparatus for measuring the concentration of a component contained in a bodily fluid in a preferred embodiment according to the present invention.

The measurement principle of the apparatus for measuring the concentration of a component contained in a bodily fluid in the present embodiment is illustrated in FIG. 1. With respect to incident light 13 which is focused on a metallic film 12 formed at the surface of a prism 11, the intensity of only incident light having a specific incident angle is reduced by the surface plasmon resonance phenomenon. A resonant angle is detected at a position 15 of a lowest intensity by measuring the intensity distribution by a light receiving element 14 at a given distance. At the same time, when the refractive index of a sample 16 as a medium adjacent to the metallic film 12 is varied, the variation is detected as a variation of the position 15 of a lowest intensity. Consequently, the concentration of a component contained in a bodily fluid can be detected based on an output from the light receiving element 14. That is to say, the concentration of substance to be measured can be detected if the resonant angle and the position can be calculated.

Figure 2:
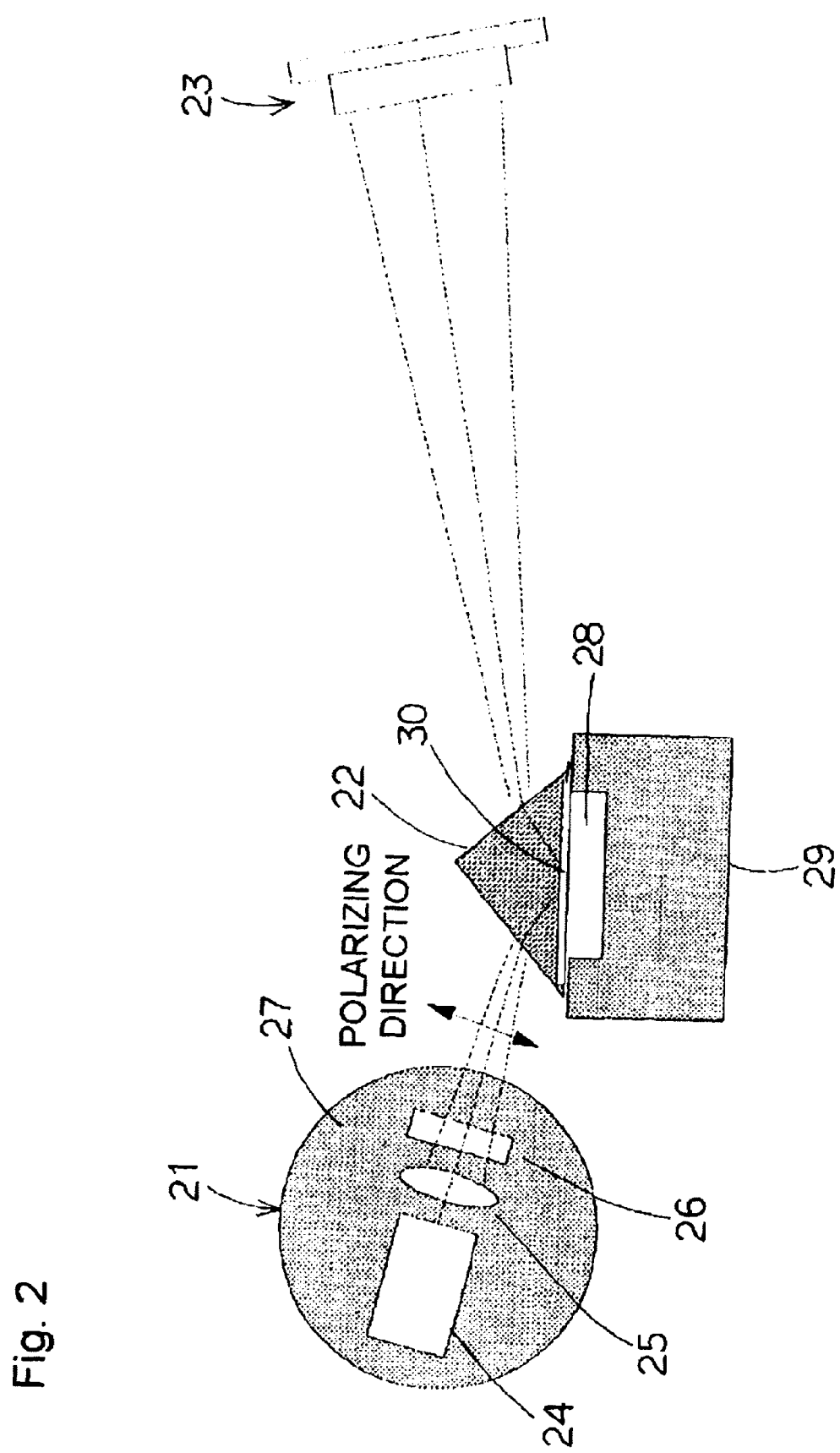
FIG. 2 is a view illustrating the configuration of an optical system in the apparatus for measuring the concentration of a component contained in a bodily fluid in the preferred embodiment.

FIG. 2 is a schematic view illustrating an optical system in the apparatus for measuring the concentration of the component contained in the bodily fluid in a preferred embodiment according to the present invention. Here, the apparatus comprises a light source 21, a prism 22 and a linear sensor array 23, which are fixed via a supporting member in such a manner as to prevent any variation of the positional relationship among the above-described members. The light source 21 includes a semiconductor laser 24 ($\lambda$=635 mm and P=3 mv), a focusing lens 25 for focusing a laser beam and a polarizing plate 26. The semiconductor laser 24, the focusing lens 25 and the polarizing plate 26 of the light source 21 are mounted on a rotary plate 27. Focusing adjustment is performed by finely adjusting the rotating angle of the rotary plate 27.

The prism 22 was mounted on a fluid holding table 29 having a sample holder 28 for holding a sample fluid to be measured at the top surface thereof. Incidentally, an optimum incident angle was about 48° in the case of air, or it was about 6° in the case of water.

Here, the laser was used as the light source. However, other light sources such as an LED and a low coherent laser may be used for the measurement since interference noise is liable to occur, although the laser beam is advantageous to the measurement in a minute region.

The prism 22 was made of BD7, and further, was provided at one surface thereof with a metallic film 30 in order to generate the surface plasmon resonance. The metallic film 30 was obtained by depositing chromium (Cr) in several nm, followed by deposition of gold (Au) in about 50 nm.

The metallic film may be made of metals such as silver (Ag) other than Cr and Au. Moreover, the metallic film may have the structure of a single layer or a plurality of layers in addition to the two-layer structure.

The linear array sensor was used as the light receiving element, for detecting a light intensity reducing position (i.e., a dark line emerging position) caused by the surface plasmon resonance. The detection channel of the linear array sensor 23 was 32 Ch, and it was arranged with a distance at which light within the range of a focusing angle of about 4° was received at about 0.17°/Ch.

The sample fluid was put into the sample holder (i.e., a groove) 28 at the upper portion of the fluid holding table 29, to be brought into contact with the bottom surface of the prism 22, and then, the dark line detecting position on the linear array sensor 23 was measured. The obtained light intensity distribution data had noise or restrictions such as the size of the linear array sensor 23 from the viewpoint of hardware. Thus, a lowest light intensity position was obtained with accuracy more enhanced by correcting an inclination or a multi-dimensional approximation.

Figure 3:
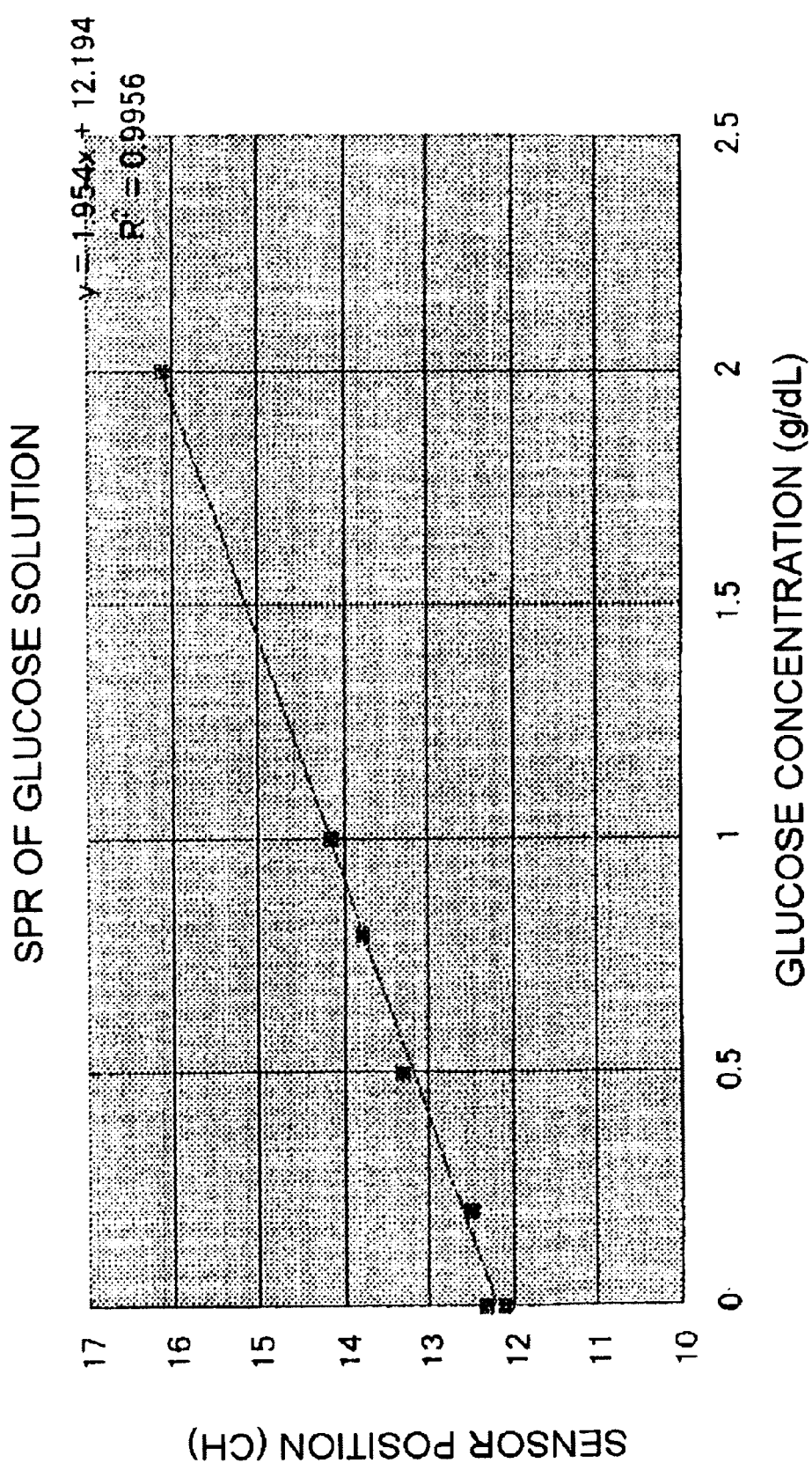
FIG. 3 is a graph illustrating the relationship between a resonant angle measured by the apparatus for measuring the concentration of a component contained in a bodily fluid in the preferred embodiment and a glucose concentration.

A glucose standard solution (within a range of a concentration from 0 to 2.0 g/dL) was produced as a solution of a sample to be measured. Measurement results by such a measuring system are shown in FIG. 3. A high correlation between a glucose concentration and a resonant angle is found in the entire region within the range of the concentration from 0 to 2.0 (g/dL). The glucose concentration can be found based on a change in resonant angle.

In the case where a measurement wavelength variable type light source is used as a measurement light source, for example, a wavelength, at which the light receiving sensitivity of one light receiving element becomes minimum, is stored while scanning the measurement wavelength in place of the detection of the change in surface plasmon resonant angle by the linear sensor array. Thus, the solvent concentration of the sample can be found based on the relationship between the wavelength and the concentration of the sample and the stored wavelength.

In place of the prism illustrated in FIG. 1, a trapezoidal element is used as the surface plasmon element, thereby suppressing the height so as to reduce the size of the element. Furthermore, a signal can be amplified by multiple reflection. Otherwise, a thinner detection element can be formed by using a diffraction grating in place of the prism.

Figure 4:
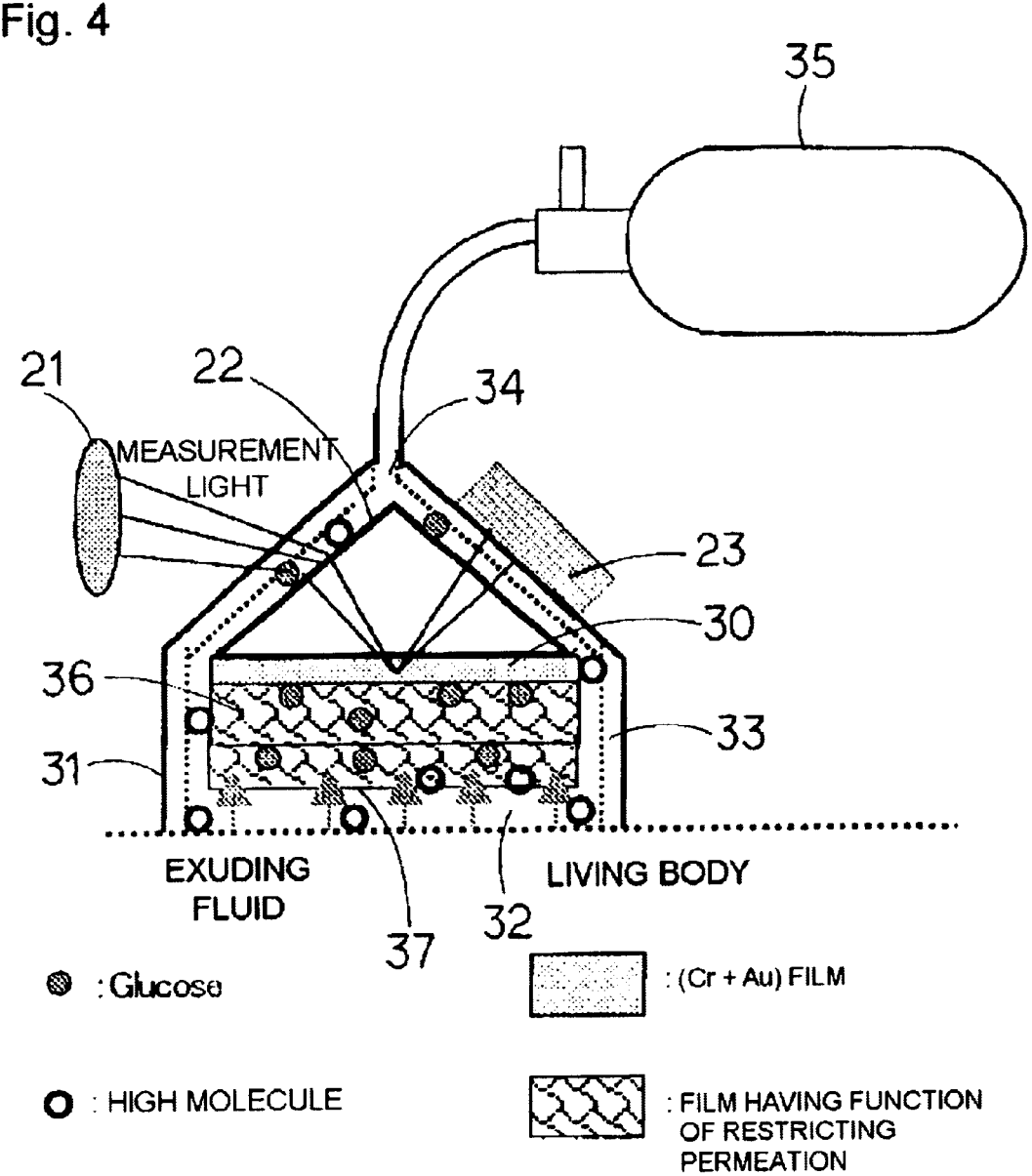
FIG. 4 is a view illustrating a measuring unit in an apparatus for measuring the concentration of a component contained in a bodily fluid in another preferred embodiment according to the present invention.

FIG. 4 is a view illustrating a measuring unit in an apparatus for measuring the concentration of a component contained in a bodily fluid in another preferred embodiment according to the present invention. A prism 22 is made of BK7 and has a bottom area of 10 * 15 mm. A metallic thin layer 30 coated with chromium (Cr) in a thickness of 5 nm and gold (Au) in a thickness of 50 nm by deposition is formed at the bottom surface of the prism 22. The prism 22 is contained inside of a glass container 31 made of the same material as that of the prism 22.

The bottom of the glass container 31, which side of the bottom surface of the prism 22 is released with a space of 100 to 200 $\mu$m apart from a skin. A part of the bottom surface of the prism 22 is fixed to the glass container 31. A pressure is reduced through a suction port 34 formed on a side opposite to the bottom surface with a clearance 33 between the prism 22 and the glass container 31 except the fixing portion.

Suction is performed by a pressure reducing tank 35 connected to the suction port 34. Since the entire system including the connecting portion, a space around the prism and the surface of the skin stays in a low pressure state owing to the communication with the pressure reducing tank 35, a subcutaneous exuding fluid can be obtained. Furthermore, a larger tank container is disposed in comparison with other space containers, so that the low pressure state can be maintained for a long period of time, and therefore, the measurement can be performed for a long period of time.

Porous molecular weight selective films for allowing the substance contained in the bodily fluid to selectively permeate therethrough according to a molecular weight are disposed in the space 32 defined between the bottom surface of the prism 22 and the skin. Here, there are provided two molecular weight selective films 36 and 37 in a dually layered manner. A quantity of subcutaneous exuding fluid is about 30 $\mu$L/h/cm$^2$/400 Toff in the case of a human being. The measurement can be performed after a lapse of about 40 sec., during which the space (h=0.15 mm, about 0.3 $\mu$L) between the skin and the released bottom surface of the prism (2 * 1 mm, 2 mm$^2$) is filled with the subcutaneous exuding fluid. Furthermore, continuous measurement can be performed since a fresh subcutaneous exuding fluid is continuously changed over by the suction.

In the case where a high molecular component contained in the subcutaneous exuding fluid such as protein or lipid adheres to the bottom surface of the prism 22 or the concentration is largely changed, a refractive index in the vicinity of the bottom surface of the prism 22 may be varied to thus induce a measurement error. In view of this, the porous molecular weight selective films 36 and 37 having the function of preventing any permeation of protein or lipid are additionally disposed at the bottom surface of the prism 22, thereby effectively maintaining and enhancing the accuracy.

For example, a fluororesin film (i.e., a film fluorine-based hydrophobic membrane such as an ion exchange membrane) or an ion complex film is suitable for the porous molecular weight selective film. The permeability of the fluororesin film can be controlled by varying a thickness, the number of layers or a heating temperature or time after coating. The permeability of the ion complex film made of an anionic or cationic solvent (which is produced by sequentially coating with polystyrene sodium sulfonate and poly-L-lysine hydrogen bromide hydrochloric acid) also can be controlled by varying a concentration or the number of coating layers.

In the case where the film having the function of preventing any permeation of protein or lipid is formed directly at the measurement surface at the bottom surface of the prism in the above-described manner, a plasmon generating region (i.e., a refractive index measuring region, a bodily fluid layer at the prism measurement surface in a thickness of about 0.1$\mu$) may not be sufficiently secured at the surface since the film is fine.

FIG. 4 illustrates an example in which a special layer is provided for securing the sufficient measurement region by allowing the bodily fluid after removal of the high molecular component such as protein or lipid from the bodily fluid to remain at the measurement surface at the bottom surface of the prism. A film having a high molecule permeability and a great space inside of the film, for example, a cellulose-based film is suitable for the special layer.

In this manner, it is effective that the porous molecular weight selective film is formed into a laminate film formed with a plurality of films different in selectiveness from each other.

From the viewpoint of the material of the film, an albumin fixing film or an etching fine pore treatment polycarbonate film may be used as the porous molecular weight selective film.

Although the description has been given of the example in which the glucose is measured by removing the high molecular substance such as protein in the above-described preferred embodiment, the glucose may be measured by obtaining, for example, the concentration of the protein.

That is to say, the refractive index of the bodily fluid is greatly attributable to glucose and protein, wherein the glucose is low molecular substance while the protein is high molecular substance. Thus, since an output from the optical element without any porous molecular weight selective film expresses the total concentration (A) of glucose and protein and an output from the optical element provided with a porous molecular weight selective film expresses the concentration (B) of only glucose when the optical element provided with the porous molecular weight selective film and the other optical element without any porous molecular weight selective film are used, the concentration of protein can be found by subtracting the value (B) from the value (A).

Although the example of the subcutaneous exuding fluid as the bodily fluid from a living body has been described already, sweat, gingival crevice fluid, blood or urine can be measured in addition to the subcutaneous exuding fluid.

Figure 5:
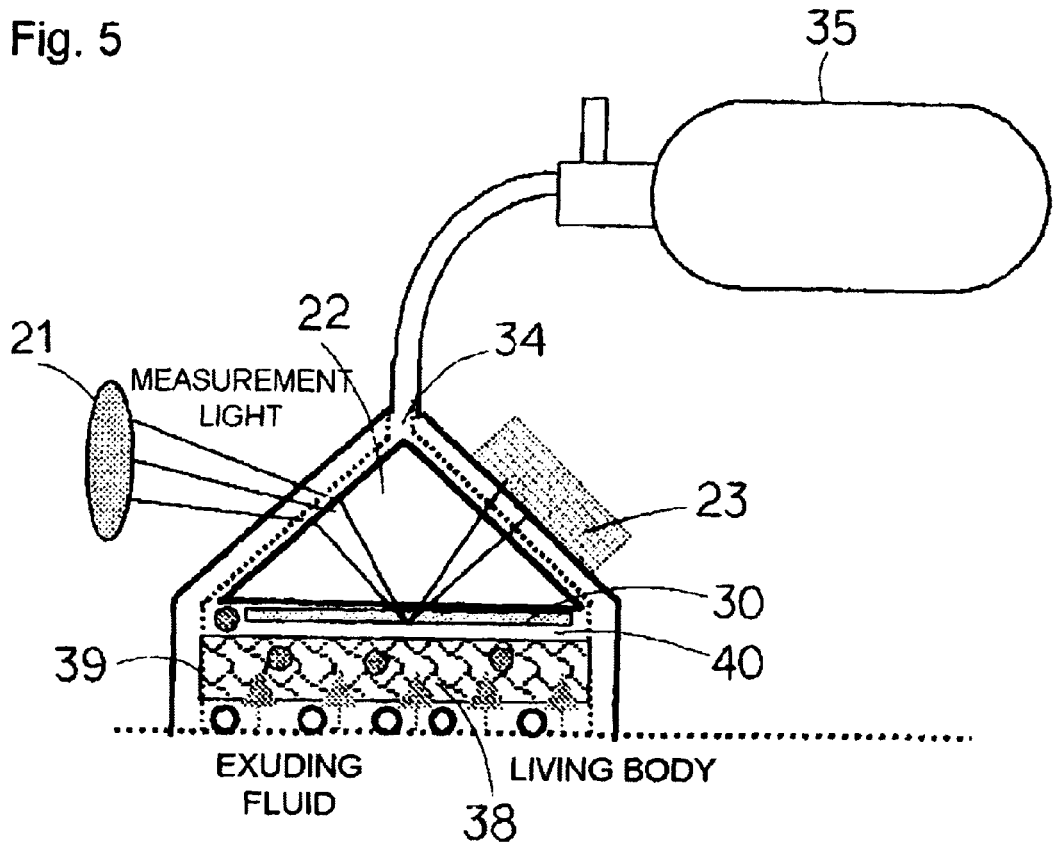
FIG. 5 is a view illustrating a measuring unit in an apparatus for measuring the concentration of a component contained in a bodily fluid in a further preferred embodiment according to the present invention.

FIG. 5 is a view illustrating a measuring unit in an apparatus for measuring the concentration of a component contained in a bodily fluid in a further preferred embodiment according to the present invention.

The present embodiment is exemplified by the case where a porous molecular weight selective film 38 is provided in addition to a surface plasmon resonance element comprising a prism 22 and a metallic film 30. The porous molecular weight selective film 38 and the metallic film 30 in the surface plasmon resonance element are arranged with a slight clearance 40 formed therebetween. The clearance 40 corresponds to the clearance of the high permeable film illustrated in FIG. 4, and exhibits the function of reserving a bodily fluid at a surface plasmon resonance generating position.

Moreover, the bodily fluid is continuously sucked to the surface of the surface plasmon element, so that measurement can be performed at a speed higher than that in the measuring method illustrated in FIG. 4.

Figure 6:
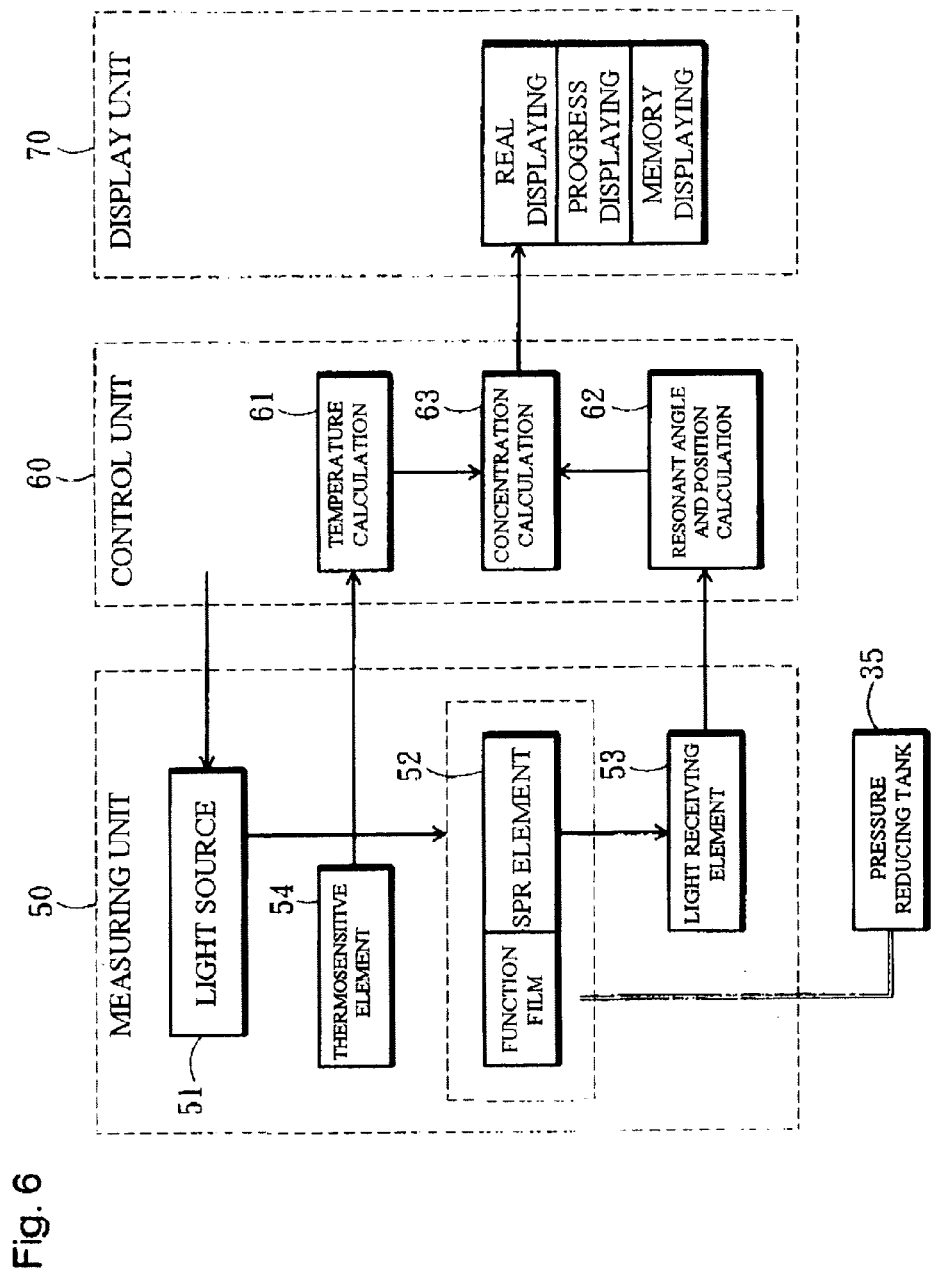
FIG. 6 is a block diagram illustrating the general configuration of the apparatus for measuring the concentration of a component contained in a bodily fluid in the preferred embodiment according to the present invention.

FIG. 6 is a block diagram illustrating the general configuration of the apparatus for measuring the concentration of the component contained in the bodily fluid in the present embodiment. The apparatus for measuring the concentration of the component contained in the bodily fluid in the present embodiment functionally comprises a measuring unit 50, a control unit 60 and a display unit 70. As described already, the measuring unit 50 includes a light source 51, a surface plasmon resonance element 52, a light receiving element 53 and a thermosensitive element 54, and further, is provided with a pressure reducing tank 35.

The control unit 60 outputs a light source control signal, and further, is provided with a temperature calculator 61, a resonant angle and position calculator 62 and a concentration calculator 63. The display unit 70 has the functions of displaying a measurement value at real time or displaying a progress, and fetching the measurement value stored in a memory so as to display it.

Figure 7:
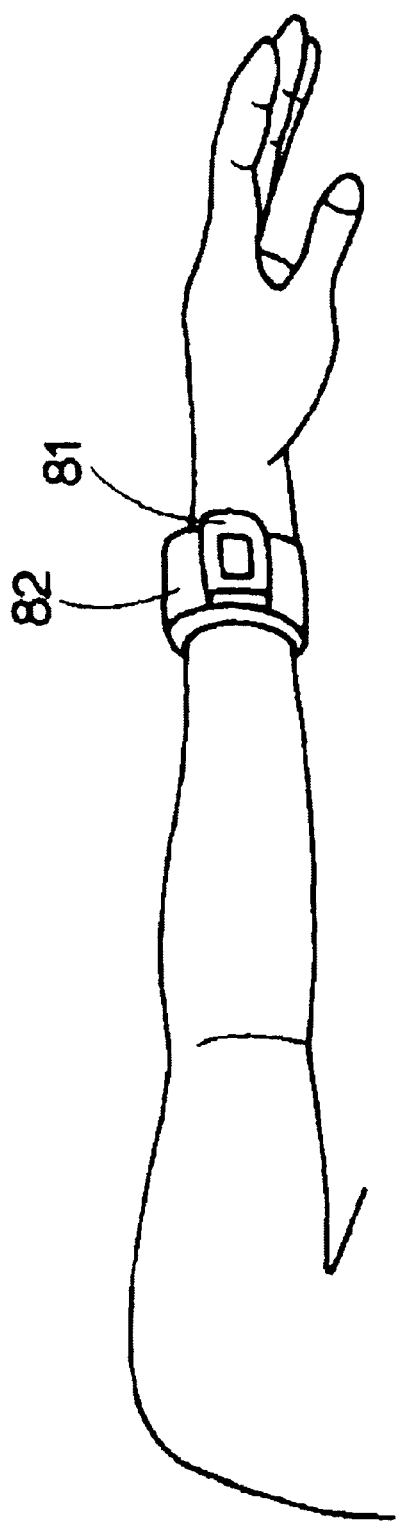
FIG. 7 is a view showing one example of the outside appearance of the apparatus for measuring the concentration of a component contained in a bodily fluid in the preferred embodiment.

The apparatus for measuring the concentration of the component contained in the bodily fluid in the present embodiment consists of a main body 81 incorporating therein the measuring unit, the control unit, the pressure reducing tank and the like and a fixing portion 82 for positioning the measuring unit between the reverse of the main body 81 and the skin, wherein the outside appearance is illustrated in FIG. 7. The apparatus is worn on a wrist.

Figure 8:
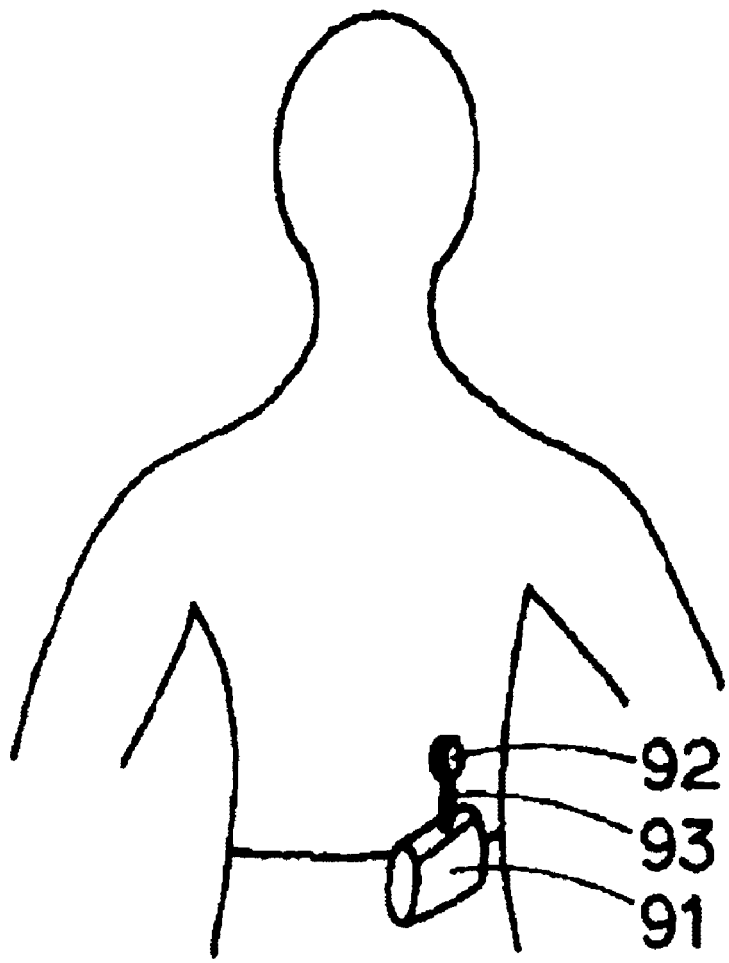
FIG. 8 is a view showing another example of the outside appearance of the apparatus for measuring the concentration of a component contained in a bodily fluid in the preferred embodiment.

Otherwise, the apparatus for measuring the concentration of the component contained in the bodily fluid in the present embodiment may consist of a main body 91 including the control unit, the display unit and the pressure reducing tank and a measuring unit 92, which are connected to each other via a wire 93 including a control cable and a suction tube, as illustrated in FIG. 8, wherein the measuring unit 92 may be brought into contact with the surface of a human body so as to hook and hold the main body 91 on a belt or the like.

Figure 9:
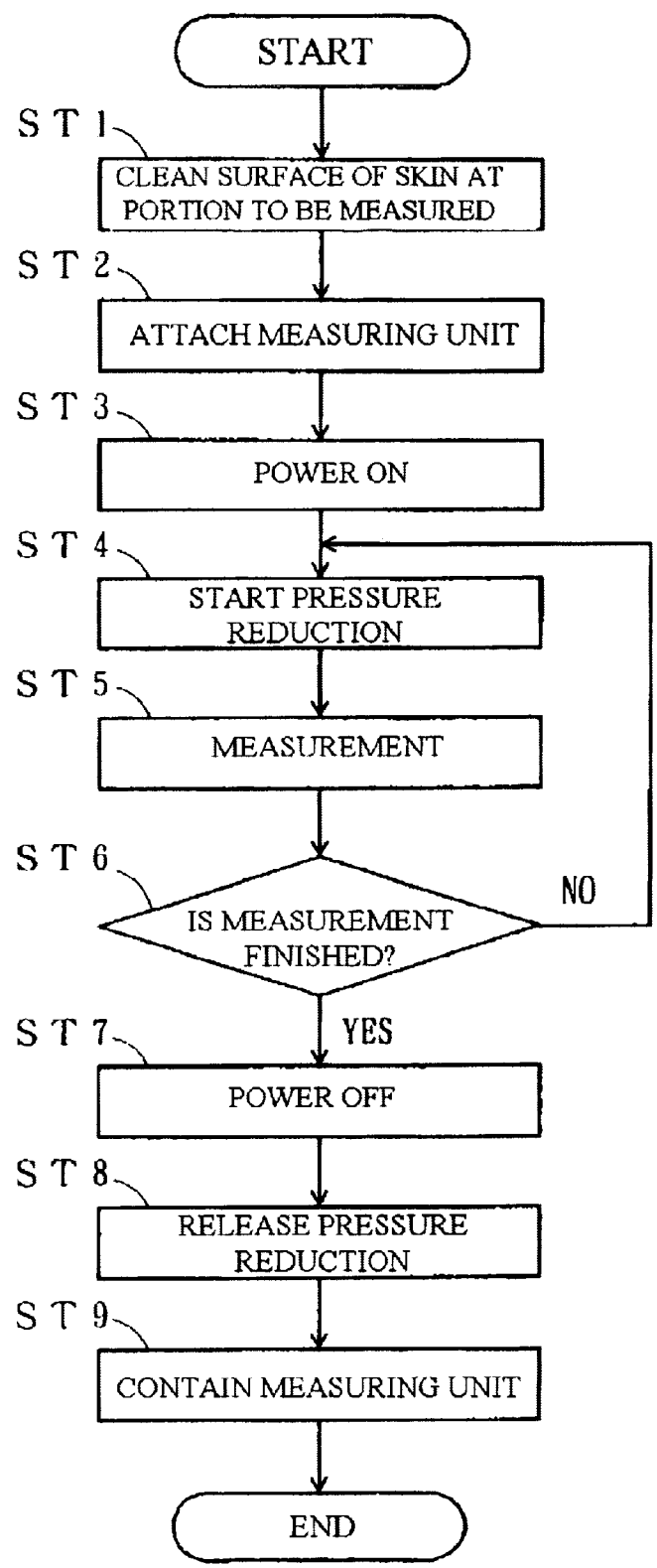
FIG. 9 is a flowchart illustrating measurement procedures by the apparatus for measuring the concentration of a component contained in a bodily fluid in the preferred embodiment.

Subsequently, measurement procedures by the apparatus for measuring the concentration of the component contained in the bodily fluid in the preferred embodiment will be explained in reference to a flowchart illustrated in FIG. 9.

First, the surface of a skin at a portion to be measured of a person to be measured is cleaned (step ST1), and then, the measuring unit is attached to the surface of the skin at the portion to be measured. For example, in the measuring apparatus illustrated in FIG. 7, the main body 81 is disposed at a predetermined position of a wrist via a belt serving as the fixing portion 82 (step ST2). Next, a power source is turned on (step ST3), and thus, the pressure at the measuring unit is started to be reduced by the pressure reducing tank 35 (step ST4). When a bodily fluid is exuded after a lapse of 20 to 40 mm sec. after the beginning of the pressure reduction, measurement is performed by the measuring unit (step ST5). Until the measurement is finished (step ST6), the routine returns to step ST4, in which the pressure reduction is maintained and the measurement is continued.

Upon completion of the measurement, the power source is turned off (step ST7), the pressure reduction is released (step ST8), and then, the measuring unit is contained, whereby the routine comes to an end (step ST9).

Figure 10:
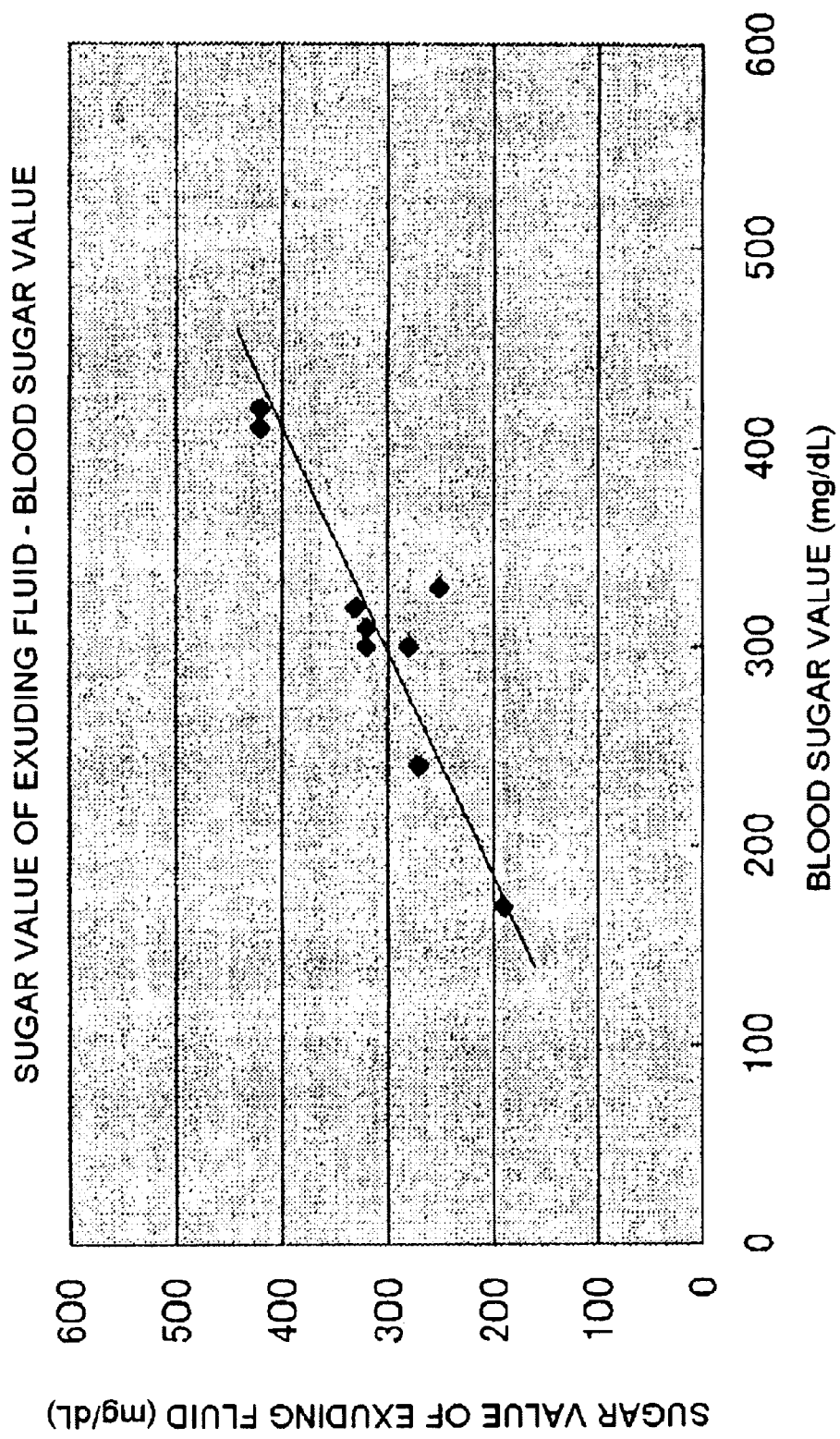
FIG. 10 is a graph illustrating the correlation between a glucose value measured by the apparatus for measuring the concentration of a component contained in a bodily fluid in the preferred embodiment and a blood sugar value of a subcutaneous exuding fluid.

The correlation between glucose values of the subcutaneous exuding fluid measured by the apparatus for measuring the concentration of the component contained in the bodily fluid in the preferred embodiment and blood sugar values measured by another method at the same time is illustrated in FIG. 10. The excellent correlation can be obtained.

A description will be given below of apparatuses for measuring the concentration of a component contained in a bodily fluid by measuring a refractive index in still further embodiments.

Figure 11:
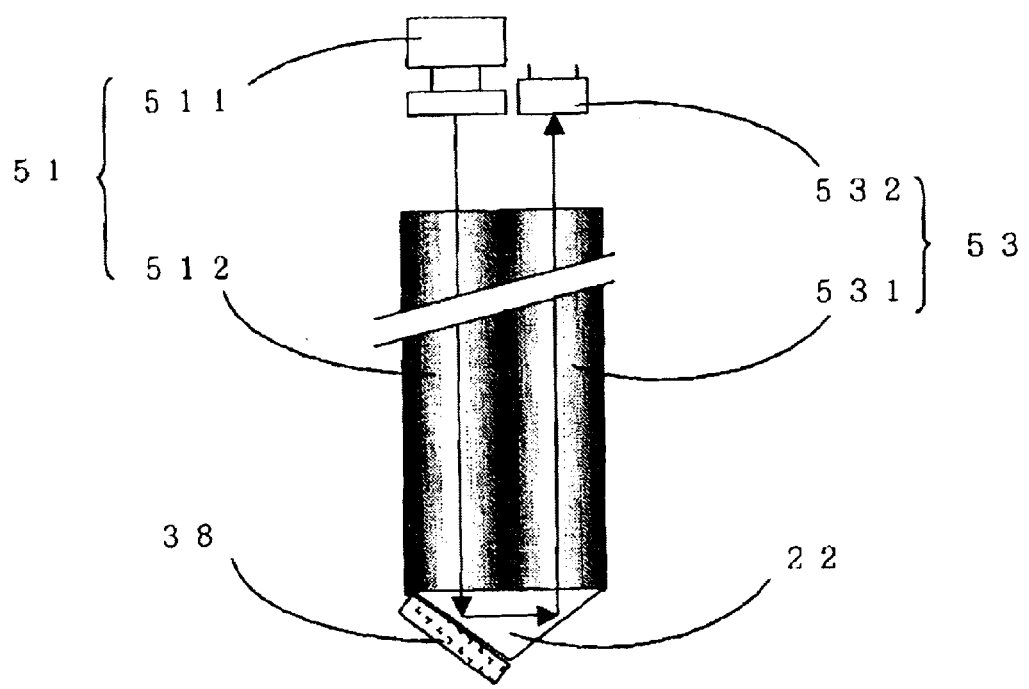
FIG. 11 is a view illustrating a measuring unit in an apparatus for measuring the concentration of a component contained in a bodily fluid in a still further preferred embodiment according to the present invention.

FIG. 11 schematically illustrates a measuring light source unit, a molecular weight selective film, a light receiving element and an optical element in an apparatus for measuring the concentration of a component contained in a bodily fluid by measuring a refractive index.

Here, a light source unit 51 includes a light source 511 and an optical fiber 512 for incidence, and further, a light receiving element 53 includes an optical fiber 531 for reflection and a light intensity measuring device 532. The optical fiber 512 for incidence and the optical fiber 531 for reflection are juxtaposed with each other, as illustrated in FIG. 11. A prism 22 serving as the optical element is disposed at the tip of the two optical fibers 512 and 531 juxtaposed with each other. A porous molecular weight selective film 38 is attached to one end surface of the prism 22. A light beam emitted from the light source enters into the prism 22 through the optical fiber 512 for incidence, and then, is reflected on at least a surface inside of the prism, to which the porous molecular weight selective film 38 is attached, and thereafter, is introduced to the light intensity measuring device 532 through the optical fiber 531 for reflection.

Incidentally, a molded product may be used as the prism 22.

By the use of the optical configuration illustrated in FIG. 11, a refractive index can be measured by measuring an absorption quantity of each of wavelengths and grasping variations in absorption wavelength according to variations in refractive index of a sample interposed between the surface of the prism and the molecular weight selective film while sequentially varying an incident wavelength from the light source. A control unit, not illustrated, calculates the concentration of substance to be measured contained in the sample based on the refractive index.

In the above-described apparatus for measuring the concentration of the component contained in the bodily fluid, it is convenient that the porous molecular weight selective film 38 is configured to be readily attached to or detached from other constituent members in the apparatus for measuring the concentration of the component contained in the bodily fluid. With such a structure, the porous molecular weight selective film 38 is thrown away after one use, and therefore, it becomes unnecessary to clean the film.

Moreover, further convenience can be achieved by configuring not only the porous molecular weight selective film 38 but also the optical element 22 in such a manner as to be readily attached to or detached from the other constituent members. A prism molded with a resin or a prism molded with glass can be used as the optical element 22 separable from the apparatus for measuring the concentration of the component contained in the bodily fluid, and further, it can be mass-produced at a reduced cost. If not only the porous molecular weight selective film 38 but also the optical element 22 are thrown away after one use, the measuring operation can be simplified.

Additionally, a description will be given below of an apparatus for measuring the concentration of a component contained in a bodily fluid in a further preferred embodiment, in which a part of an outside case and a molecular weight selective film in the apparatus for measuring the concentration of the component contained in the bodily fluid are transparent.

Figure 12A:
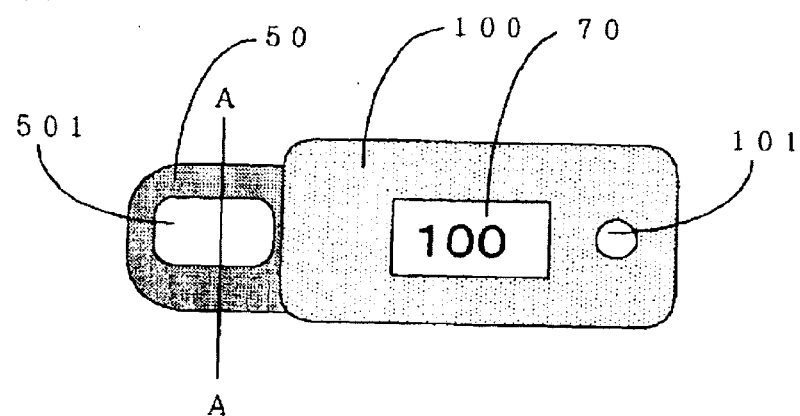
FIGS. 12A and 12B are a view showing a further example of the outside appearance of the apparatus for measuring the concentration of a component contained in a bodily fluid in the preferred embodiment and a cross-sectional view showing the same, respectively.
Figure 12B:
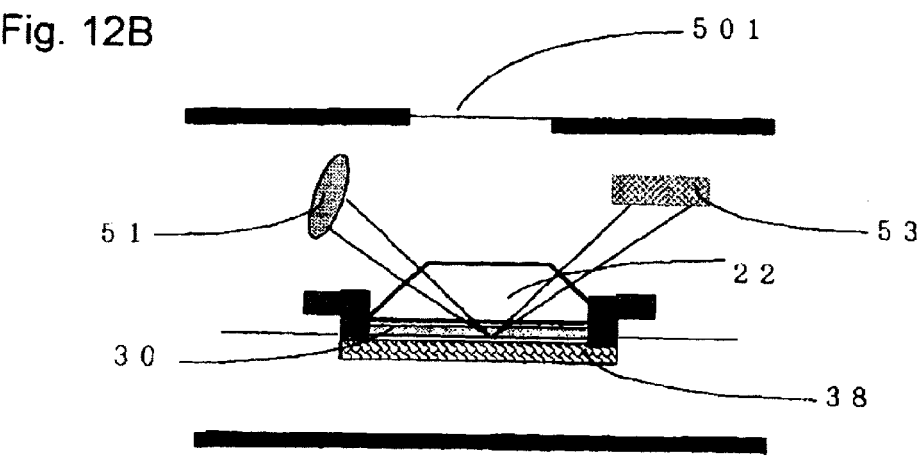

FIG. 12A shows the outside appearance of the apparatus for measuring the concentration of the component contained in the bodily fluid in which a part of an outside case and a molecular weight selective film are transparent; and FIG. 12B schematically illustrates the cross section taken along a line A—A of FIG. 12A.

As shown in FIG. 12A, the apparatus for measuring the concentration of the component contained in the bodily fluid comprises a main body 100 and a measuring unit 50. The main body 100 includes a display unit 70 and a power switch 101. The measuring unit 50 has a transparent portion 501 at a part of a case. Inside of the measuring unit are incorporated a light source 51 such as an LED (in which a focusing lens or the like is not illustrated), a trapezoidal prism 22 as an optical element, and a light receiving element 53 such as a CCD. A metallic film 30 is stuck to the bottom surface of the trapezoidal prism 22. A molecular weight selective film 38 is provided with a slight clearance defined between the prism 22 and the metallic film 30.

In the present embodiment, a part of the case above the trapezoidal prism 22 (i.e., the transparent portion 501) and the molecular weight selective film 38 are transparent. With this configuration, the exudation of a bodily fluid from the surface of a living body or the transparent condition of the bodily fluid through the molecular weight selective film can be visually observed, and therefore, the measurement can be performed while confirming the state of a very small quantity of sample to be measured.

Subsequently, a still further embodiment will be described below with respect to a light source for measurement and a light receiving element in an apparatus for measuring the concentration of a component contained in a bodily fluid according to the present invention.

Figure 13:
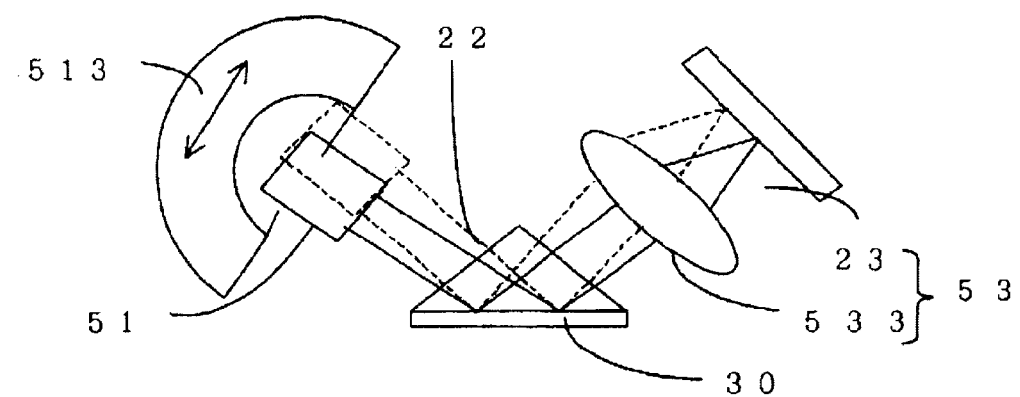
FIG. 13 is a view illustrating a light source unit for measurement and a light receiving element in an apparatus for measuring the concentration of a component contained in a bodily fluid in a still further preferred embodiment according to the present invention.

FIG. 13 schematically shows a light source unit 51 for measurement and a light receiving element 53. The light source unit 51 for measurement includes a light source for emitting parallel light beams and incident angle varying means 513 for varying the incident angles of the parallel light beams. The light receiving element 53 is constituted of a focusing lens 533 for focusing a reflected light beam and a linear array 23.

Since the entire bottom surface having a metallic film 30 of an optical element such as a prism stuck thereto can be irradiated with the parallel light beams emitted from the light source by the use of the above-described light source unit for measurement and light receiving element, even if no sample to be measured exists at a part of the bottom surface having the metallic film 30 of the prism stuck thereto or the position or quantity of sample to be measured is varied per measurement, there can be produced an effect that the measurement can be securely performed.

A still further embodiment will be described below with respect to the light source unit for measurement and the light receiving element in the above-described apparatus for measuring the concentration of the component contained in the bodily fluid according to the present invention.

Figure 14:
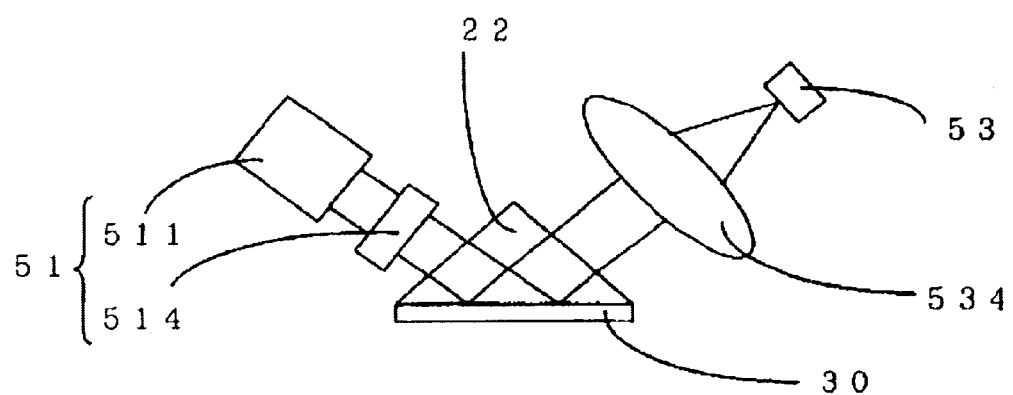
FIG. 14 is a view illustrating a light source unit for measurement and a light receiving element in an apparatus for measuring the concentration of a component contained in a bodily fluid in a still further preferred embodiment according to the present invention.

FIG. 14 is a schematic view showing a light source unit 51 for measurement and a light receiving element 53 in a still further embodiment. The light source unit 51 for measurement includes a light source 511 for emitting parallel light beams and wavelength varying means 514 for varying a wavelength. The light receiving element 53 includes a focusing lens 534 for focusing a reflected light beam. Like in the measurement of a surface plasmon resonance point based on the variation in resonant angle, a wavelength, at which a received light intensity becomes minimum at the time when the wavelength is scanned, is varied according to the concentration of substance to be measured by the use of the above-described light source unit 51 for measurement and light receiving element 53, so that the concentration of the substance to be measured can be measured by observing the wavelength of the minimum received light intensity. As the wavelength varying means may be used a laser or an LED without any variation in supplied current or a diffraction grating or a filter having a wavelength separating function.

Consequently, the light source unit 51 for measurement need not vary an incident angle, and therefore, it has no movable member, whereby its configuration becomes simple. Furthermore, the light receiving element 53 is a single light receiving element such as a photodiode or a photo transistor, and therefore, it is simple in configuration and low in cost.

A description will be given below of one example in a still further embodiment in which reverse iontophoresis is adopted in a bodily fluid taking unit in an apparatus for measuring the concentration of a component contained in a bodily fluid according to the present invention.

Figure 15A:
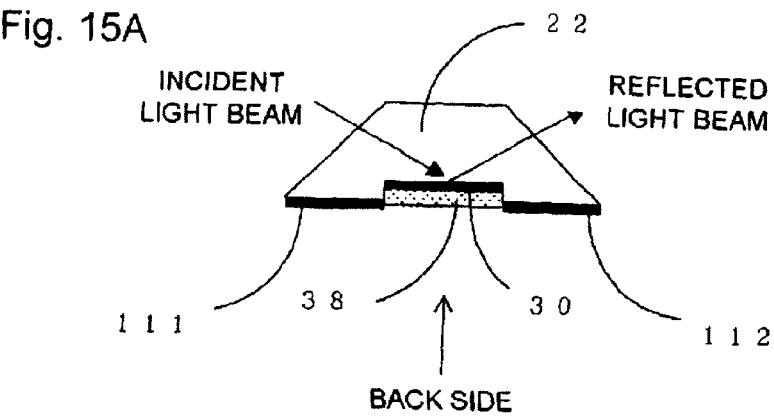
FIGS. 15A to 15C are views illustrating a bodily fluid taking unit in an apparatus for measuring the concentration of a component contained in a bodily fluid in a still further preferred embodiment according to the present invention.
Figure 15B:
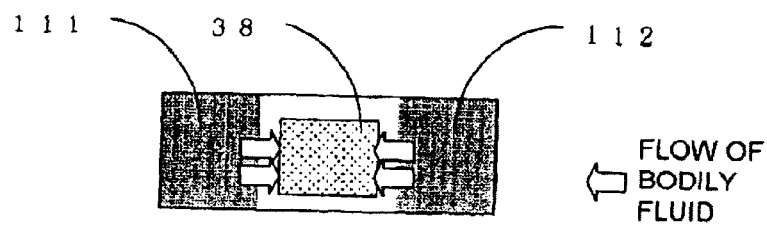

FIG. 15A is a schematic view showing an optical element in which reverse iontophoresis is used as a bodily fluid taking method; and FIG. 15B is a schematic view showing the optical element viewed from the bottom surface thereof in a B direction. A prism 22 is adopted as the optical element. A pair of electrodes 111 and 112 for the reverse iontophoresis are disposed at the bottom surface of the prism 22, and further, a metallic film 30 for reflecting an incident light beam and a porous molecular weight selective film 38 are interposed between the pair of electrodes 111 and 112 in a dually layered manner. As found from FIG. 15A, the metallic film 30 is disposed more deeply in the prism 22, and the porous molecular weight selective film 38 and the pair of electrodes 111 and 112 for the reverse iontophoresis are flush with each other at the bottom surface of the prism 22. A subcutaneous exuding fluid is induced together with the movement of ions with the application of a DC potential to between the pair of electrodes 111 and 112 for the reverse iontophoresis, and then, is exuded to the surface of a skin between the pair of electrodes. A current quantity is variably controlled in such a manner as to become constant by holding a potential between the pair of electrodes for the reverse iontophoresis at a constant value or reversing the polarity per given period of time, so that a bodily fluid can be exuded from under the skin. The subcutaneous exuding fluid penetrates into the porous molecular weight selective film 38, by which the subcutaneous exuding fluid is selected, and then, is exuded out as a sample to be measured in a clearance defined between the metallic film 30 and the porous molecular weight selective film 38.

Figure 15C:
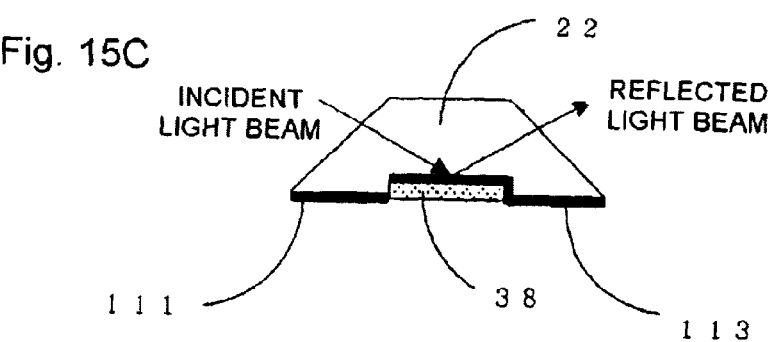
Figure 16:
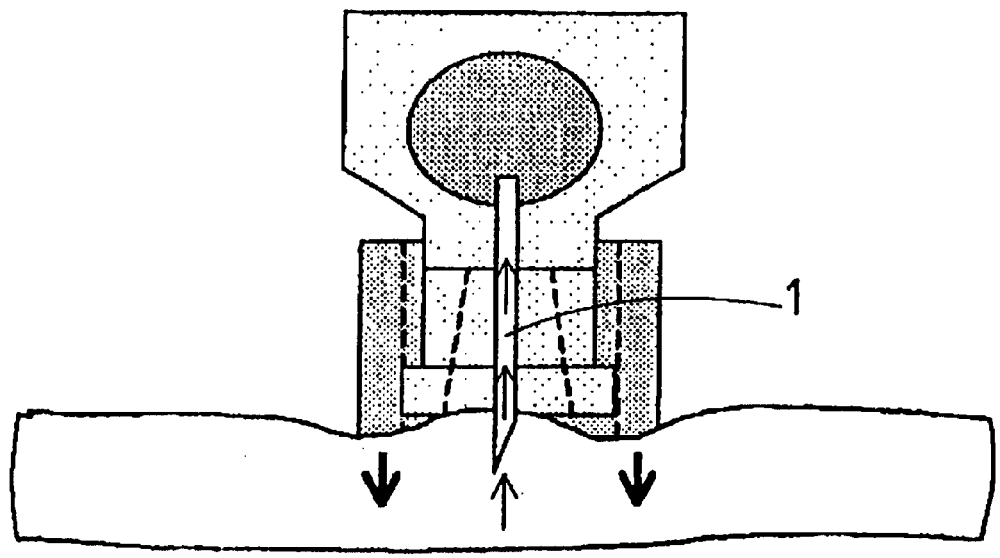
FIG. 16 is a view illustrating a method for taking a subcutaneous bodily fluid by means of a small-sized syringe needle in the prior art.
Figure 17A:
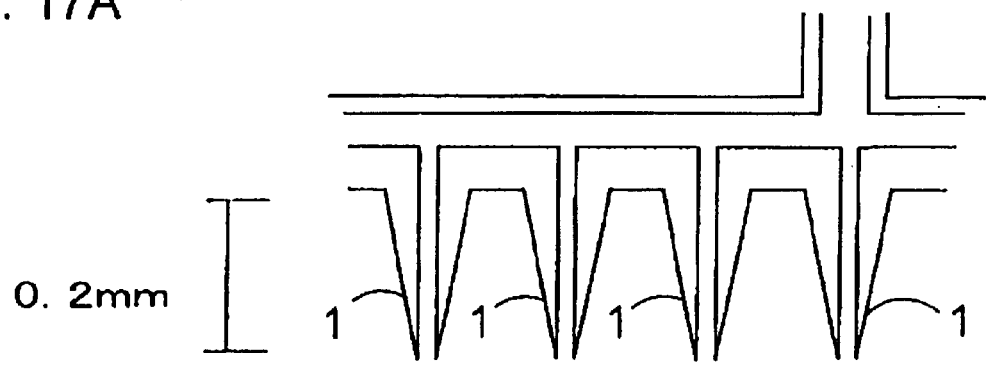
FIGS. 17A and 17B are views illustrating a method for taking a subcutaneous bodily fluid by means of a plurality of small-sized syringe needles in the prior art.
Figure 17B:
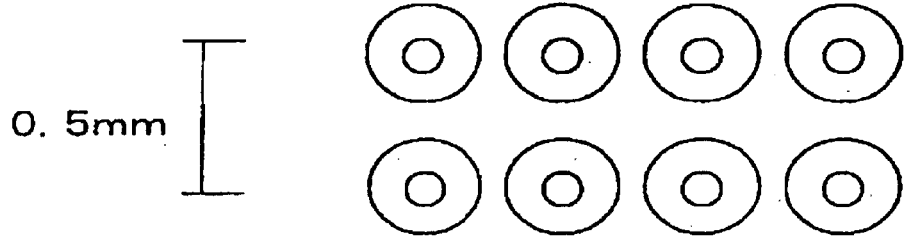

With this constitution, the metallic film and one of the electrodes for the reverse iontophoresis are used together, thereby achieving a common structure 113, as shown in FIG. 15C. Since the generation of a difference in potential from a living body or a current in the electrode for the reverse iontophoresis cannot adversely influence on optical permeability of the prism serving as the optical element or a refractive index of substance to be measured, the common use of them cannot raise any problem. The common structure 113 constituted of the metallic film and one of the electrodes for the reverse iontophoresis can not only simplify the configuration but also allow the subcutaneous exuding fluid to exude into the clearance defined between the common structure 113 as the metallic film and the molecular weight selective film 38 without any loss, thereby shortening a measurement time and reducing a quantity of sample to be measured.

Since the bodily fluid is taken by the pressure reduction or the reverse iontophoresis according to the present invention, a quantity of bodily fluid to be taken is remarkably small, a physical or mental pain suffered by a test subject can be reduced in comparison with a blood taking method. The taken subcutaneous exuding fluid need not be diluted. Furthermore, since the taken subcutaneous exuding fluid does not contain any blood cell therein, it can be readily measured for a long period of time even without any special treatment such as anticoagulation treatment.

Moreover, since a very small quantity of sample can be gradually and continuously obtained, the continuous measurement can be performed. Additionally, the mechanisms or parts for securing a given quantity of sample are provided at a low cost.

In addition, since the refractive index is measured by the use of, in particular, the surface plasmon resonance element, the sample can be measured in a very small quantity with a rapid response of a measurement output. The measurement can be performed one by one or continuously. Since the optical part can be recycled, the number of consumables is reduced. Thus, there can be produced effects such as a low cost and a low load on the environment.

Furthermore, since the measurement is performed in the sealed space, a danger of infection is slight. Moreover, the exuding efficiency can be enhanced by removing stratum corneum at the surface of the skin at the taking portion in taking the subcutaneous exuding fluid.

As is clear from the above description, according to the present invention, the concentration of the biometric component contained in the sample in a very small quantity can be measured without little pain by taking the bodily fluid by the pressure reduction or the reverse iontophoresis and measuring the refractive index of the sample to be measured, which is separated from the bodily fluid, by, in particular, the surface plasmon resonance, thus remarkably reducing a burden on a test subject or a patient. Furthermore, the concentration of the biometric component is continuously measured, so that clinically significant data can be provided, thus greatly contributing to diagnosis or treatment.

What is claimed is:

1. A method for measuring the concentration of a component contained in a bodily fluid comprising the steps of:
    taking a bodily fluid from a living body;
    separating a sample to be measured from said bodily fluid taken in said bodily fluid taking step;
    measuring the refractive index of said sample separated in said sample separating step; and
    calculating the concentration of substance to be measured contained in said sample to be measured or said bodily fluid based on said refractive index measured in said refractive index measuring step,
    wherein a porous molecular weight selective film for allowing the substance contained in said bodily fluid to selectively permeate therethrough is used in said sample separating step.

2. A method for measuring the concentration of a component contained in a bodily fluid as claimed in claim 1, wherein said bodily fluid is selected from the group consisting of a subcutaneous exuding fluid, sweat, a gingival crevice fluid, blood and urine.

3. A method for measuring the concentration of a component contained in a bodily fluid as claimed in claim 1, wherein either one or both of pressure reduction and reverse iontophoresis are used in said bodily fluid taking step.

4. A method for measuring the concentration of a component contained in a bodily fluid as claimed in claim 1, wherein said porous molecular weight selective film is a laminated film in which a plurality of films different in selectiveness from each other are laminated one on another.

5. A method for measuring the concentration of a component contained in a bodily fluid as claimed in claim 1 or claim 4, wherein said porous molecular weight selective film is one film or a plurality of films selected from the group consisting of a fluororesin film, a cellulose-based film, an ion complex film, an albumin fixing film and an etching fine pore treatment polycarbonate film.

6. A method for measuring the concentration of a component contained in a bodily fluid as claimed in claim 1, wherein surface plasmon resonance is used in said refractive index measuring step.

7. A method for measuring the concentration of a component contained in a bodily fluid as claimed in claim 1, wherein the substance to be measured contained in said sample or said bodily fluid is either one or both of glucose and protein.

8. An apparatus for measuring the concentration of a component contained in a bodily fluid comprising:

a light source unit for measurement including at least a light source;

a porous molecular weight selective film which is brought into close contact with the surface of a living body;

a bodily fluid taking unit for allowing a bodily fluid to be exuded from said surface of the living body, and then, to permeate through said porous molecular weight selective film, thus obtaining a sample to be measured;

an optical element for allowing light emitted from said light source unit for measurement to enter into said sample to be measured on said porous molecular weight selective film, and further, for reflecting said light on said sample to be measured;

a light receiving element for receiving said light reflected on said sample to be measured, emitted from said optical element;

a control unit including a concentration calculator for calculating the concentration of substance to be measured contained in said sample or said bodily fluid in response to a signal output from said light receiving element; and a display unit for displaying said concentration obtained by said concentration calculator.

9. An apparatus for measuring the concentration of a component contained in a bodily fluid as claimed in claim 8, wherein said optical element is a surface plasmon element having a metallic film at a surface opposite to said porous molecular weight selective film.

10. An apparatus for measuring the concentration of a component contained in a bodily fluid as claimed in claim 8 or claim 9, wherein said light source is a laser.

11. An apparatus for measuring the concentration of a component contained in a bodily fluid as claimed in claim 8 or claim 9, wherein said light source is an LED.

12. An apparatus for measuring the concentration of a component contained in a bodily fluid as claimed in claim 9, wherein said light source unit for measurement includes a polarizing plate for polarizing the light emitted from said light source.

13. An apparatus for measuring the concentration of a component contained in a bodily fluid as claimed in claim 9, wherein said concentration calculator calculates a resonant angle and a position in response to the signal sent from said light receiving element, so as to calculate said concentration of the substance to be measured.

14. An apparatus for measuring the concentration of a component contained in a bodily fluid as claimed in claim 8 or claim 9, wherein said porous molecular weight selective film, or said porous molecular weight selective film and said optical element can be separated from the main body of the apparatus for measuring the concentration of a component contained in a bodily fluid.

15. An apparatus for measuring the concentration of a component contained in a bodily fluid as claimed in claim 8 or claim 9, further comprising a case for covering said light source unit for measurement, said porous molecular weight selective film, said optical element and said light receiving element, wherein a part of said case and said porous molecular weight selective film are transparent, so that exudation of said bodily fluid from said surface of the living body or the state in which said bodily fluid permeates through said porous molecular weight selective film can be visually checked.

16. An apparatus for measuring the concentration of a component contained in a bodily fluid as claimed in claim 9, wherein said light source unit for measurement includes a light source for emitting parallel light beams, incident angle varying means for varying the incident angle of said parallel light beam, a focusing lens and a linear array.

17. An apparatus for measuring the concentration of a component contained in a bodily fluid as claimed in claim 9, wherein said light source unit for measurement includes a light source for emitting parallel light beams, wavelength varying means for varying the wavelength of said parallel light beam and a focusing lens.

18. An apparatus for measuring the concentration of a component contained in a bodily fluid as claimed in claim 9, wherein said bodily fluid taking unit adopts reverse iontophoresis, and said metallic film of the surface plasmon element and one of electrodes for the reverse iontophoresis are used commonly with each other.

* * * * *